United States Patent
Kawashima et al.

(10) Patent No.: US 8,895,680 B2
(45) Date of Patent: *Nov. 25, 2014

(54) REDOX CURING-TYPE NONAQUEOUS CURABLE COMPOSITION

(75) Inventors: Mitsunobu Kawashima, Kurashiki (JP); Aki Takase, Mainz (DE)

(73) Assignee: Kuraray Noritake Dental Inc., Kurashiki-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/659,805

(22) PCT Filed: Aug. 8, 2005

(86) PCT No.: PCT/JP2005/014502
§ 371 (c)(1), (2), (4) Date: Feb. 9, 2007

(87) PCT Pub. No.: WO2006/016545
PCT Pub. Date: Feb. 16, 2006

(65) Prior Publication Data
US 2008/0081889 A1    Apr. 3, 2008

(30) Foreign Application Priority Data
Aug. 9, 2004  (JP) ................. 2004-232731

(51) Int. Cl.
*C08F 4/40* (2006.01)
*C08F 4/28* (2006.01)
*C08F 4/00* (2006.01)
*C08F 2/00* (2006.01)
*C09K 3/00* (2006.01)
*A61L 24/04* (2006.01)

(52) U.S. Cl.
CPC .. *C08F 4/40* (2013.01); *A61L 24/04* (2013.01)
USPC ...... 526/181; 526/227; 526/234; 252/182.12; 252/182.18; 252/183.13

(58) Field of Classification Search
USPC ........... 252/182.12, 182.18, 183.12, 1, 8, 10, 252/12, 14, 26–27, 29–39; 526/181, 227, 526/234
See application file for complete search history.

(56) References Cited

U.S. PATENT DOCUMENTS

| | | | |
|---|---|---|---|
| 4,446,246 A | | 5/1984 | McGinniss |
| 4,499,251 A | * | 2/1985 | Omura et al. ............... 526/278 |
| 4,540,722 A | * | 9/1985 | Bunker ..................... 523/109 |
| 4,849,138 A | * | 7/1989 | Onoe et al. ................ 562/125 |
| 6,214,101 B1 | * | 4/2001 | Nakaseko .................... 106/35 |
| 2003/0018098 A1 | * | 1/2003 | Falsafi et al. ................ 523/116 |

FOREIGN PATENT DOCUMENTS

| | | |
|---|---|---|
| EP | 0 061 240 A2 | 9/1982 |
| EP | 0061240 A2 * | 9/1982 |
| GB | 1 540 739 | 2/1979 |
| JP | 45-29195 | 9/1970 |
| JP | 52 39782 | 3/1977 |
| JP | 53-39331 | 4/1978 |
| JP | 53-67740 | 6/1978 |
| JP | 54-11149 | 1/1979 |
| JP | 57 168903 | 10/1982 |
| JP | 58-21687 | 2/1983 |
| JP | 58-125710 | 7/1983 |
| JP | 59 89304 | 5/1984 |
| JP | 61-296077 | 12/1986 |
| JP | 61 296077 | 12/1986 |
| JP | 62-100566 | 5/1987 |
| JP | 62 100566 | 5/1987 |
| JP | 62-175410 | 8/1987 |
| JP | 6-40835 | 2/1994 |
| JP | 6-40838 | 2/1994 |

OTHER PUBLICATIONS

MSDS of sodium sulfite; Solvay Chemicals; Oct. 6, 2003.*
Material Safety Data Sheet (sodium sulfite), http://www.vekoy.com/UserFiles/File/PDF-liitteet/KT-SODIUM.pdf, Oct. 2005.*

* cited by examiner

*Primary Examiner* — Karuna P Reddy
(74) *Attorney, Agent, or Firm* — Oblon, Spivak, McClelland, Maier & Neustadt, L.L.P.

(57) ABSTRACT

The present invention relates to redox-curing type nonaqueous curable compositions having: at least one liquid radical polymeric monomer (a); an organic peroxide (b); and a powdered water-soluble reducing compound (c), where the powdered water-soluble reducing compound (c) is dispersed in the liquid radical polymeric monomer (a).

16 Claims, No Drawings

REDOX CURING-TYPE NONAQUEOUS CURABLE COMPOSITION

CROSS-REFERENCE TO RELATED APPLICATION

This application is a 371 of PCT/JP05/014502, filed on Aug. 8, 2005, and claims prioriy to Japanese Patent Application No. 2004-232731, filed Aug. 9, 2004.

TECHNICAL FIELD

The present invention relates to a redox-curing type nonaqueous curable composition, and more particularly, it relates to a redox-curing type nonaqueous curable composition whose curing reaction is accelerated through a contact with a wetting material including moisture (hereinafter simply referred to as a "wetting material").

BACKGROUND ART

An adhesive material is used for healing/treating wetting materials like biological hard tissues such as teeth and bones. As an adhesive material used for a wetting material, a resin-based curable composition including a radical polymeric monomer, a polymerization initiator and so on is generally used.

Means for improving the adhesive property of the resin-based curable composition against a wetting material and more particularly a biological hard tissue is conventionally roughly divided into the following two proposals: One of the proposals relates to a radical polymeric monomer including an acidic group for improving the chemical/physical interaction with a matrix of a tooth, a bone or the like to be adhered (see Patent Documents 1 through 3 below), and the other relates to a polymerization initiator for efficiently polymerically curing, on a biological hard tissue, a curable composition including a radical polymeric monomer having an acidic group (see Patent Documents 4 through 6 below).

When the resin-based curable composition is adhered onto a wetting material, sufficient adhesive strength is not attained due to curing inhibition caused by oxygen present on the adhesion interface in many cases. Such curing inhibition conspicuously occurs particularly when a curable composition is adhered onto a dentine of a tooth or a bone including a large amount of oxygen.

Therefore, in order to accelerate the polymeric curing reaction by suppressing the curing inhibition caused by oxygen included in a wetting material, use of a redox polymerization initiator including a catalyst (an oxidant) and an accelerator (a reductant) has been proposed. As the accelerator, a reducing compound including sulfur is particularly regarded promising (see Patent Documents 7 through 10 below).

For example, Patent Document 9 below describes a redox-curing type aqueous polymeric composition including a first agent composed of water-containing ethanol, sulfite, tertiary amine and so on and a second agent composed of a free-radical polymeric liquid monomer and a catalyst. Also, Patent Document 10 below describes a redox-curing type aqueous dental adhesive composition including a first agent composed of a polymeric phosphorus compound, a polymerization catalyst and a diluent, a second agent composed of aqueous ethanol, a sulfur compound and tertiary amine and a third agent composed of aqueous ethanol and a soluble metal salt such as $FeCl_3$. Such a divided redox-curing type aqueous curable composition is used after mixing the divided respective agents into one mixed agent.

Patent Document 1: Japanese Laid-Open Patent Publication No. Sho 53-67740
Patent Document 2: Japanese Laid-Open Patent Publication No. Sho 54-11149
Patent Document 3: Japanese Laid-Open Patent Publication No. Sho 58-21687
Patent Document 4: Japanese Laid-Open Patent Publication No. Sho 45-29195
Patent Document 5: Japanese Laid-Open Patent Publication No. Sho 53-39331
Patent Document 6: Japanese Laid-Open Patent Publication No. Sho 62-175410
Patent Document 7: Japanese Laid-Open Patent Publication No. Hei 06-40835
Patent Document 8: Japanese Laid-Open Patent Publication No. Hei 06-40838
Patent Document 9: Japanese Laid-Open Patent Publication No. Sho 57-168903
Patent Document 10: Japanese Laid-Open Patent Publication No. Sho 58-125710

DISCLOSURE OF INVENTION

Problems to be Solved by Invention

When the conventional redox-curing type aqueous curable composition disclosed in Patent Document 9 or 10 includes a large amount of accelerator such as sulfite or tertiary amine for improving the adhesive strength against a wetting material, the redox reaction (oxidation/reduction reaction) is proceeded so rapidly that the work time becomes extremely short, and such a composition cannot be practically used. On the other hand, when the content of the accelerator is suppressed to be small for securing time necessary for adhesion, the composition cannot be sufficiently cured and hence the adhesive strength against a wetting material is degraded.

Therefore, the present inventors have earnestly made various examinations for solving the antinomic problem of the conventional redox-curing type aqueous curable compositions, resulting in finding the following: The polymerization inhibition caused by oxygen is a phenomenon occurring not within a curable composition but on the adhesion interface with a wetting material, and therefore, when the redox reaction is selectively accelerated merely on the adhesion interface where the polymerization inhibition occurs, the adhesive strength against a wetting material can be improved without largely reducing the work time.

The present invention was devised on the basis of the aforementioned finding, and an object of the invention is providing a redox-curing type curable composition capable of securing time necessary for adhesion and exhibiting high adhesive strength against a wetting material and more particularly a biological hard tissue such as a dentine.

Means for Solving Problems

For achieving the object, the redox-curing type nonaqueous curable composition according to Claim 1 of the invention includes a liquid radical polymeric monomer (a), an organic peroxide (b) and a powdered water-soluble reducing compound (c), and the powdered water-soluble reducing compound (c) is dispersed in the liquid radical polymeric monomer (a).

According to Claim 2 of the invention, the powdered water-soluble reducing compound (c) of Claim 1 is a sulfite powder.

According to Claim 3 of the invention, the redox-curing type nonaqueous curable composition of Claim 1 includes 0.05 through 10 parts by weight of the organic peroxide (b) and 0.01 through 15 parts by weight of the powdered water-soluble reducing compound (c) based on 100 parts by weight of the liquid radical polymeric monomer (a).

According to Claim 4 of the invention, the redox-curing type nonaqueous curable composition of Claim 1 is dividedly packed as a first agent including the liquid radical polymeric monomer (a) and the organic peroxide (b) and a second agent including the liquid radical polymeric monomer (a) and the powdered water-soluble reducing compound (c).

According to Claim 5 of the invention, the powdered water-soluble reducing compound (c) of Claim 4 is a sulfite powder.

According to Claim 6 of the invention, in the redox-curing type nonaqueous curable composition of Claim 4, the first agent includes 0.1 through 50 parts by weight of the organic peroxide (b) based on 100 parts by weight of the liquid radical polymeric monomer (a), the second agent includes 0.1 through 50 parts by weight of the powdered water-soluble reducing compound (c) based on 100 parts by weight of the liquid radical polymeric monomer (a), and the first agent and the second agent are dividedly packed in a weight ratio of 1:10 through 10:1.

Hereinafter, the redox-curing type nonaqueous curable composition according to any of Claims 1 through 6 may be generically designated as the present composition.

According to Claim 7 of the invention, the redox-curing type nonaqueous curable composition of any of Claims 1 through 6 is used as an adhesive for a biological hard tissue.

Effects of Invention

The present invention provides a redox-curing type non-aqueous curable composition capable of securing time necessary for adhesion and exhibiting high adhesive strength against a wetting material and more particularly a biological hard tissue such as a dentine. The reasons for these effects are understood as follows:

Since the polymerization inhibition is caused by oxygen on an adhesion interface between a redox-curing type curable composition and a wetting material, the polymeric curing property is lower on the adhesion interface than within the composition. When a conventional aqueous curable composition includes a large amount of water-soluble reducing compound for improving the polymeric curing property attained on the adhesion interface, the polymeric curing property is simultaneously improved within the composition where there is no need to improve the polymeric curing property, and therefore, the curing time of the whole composition becomes too short to secure time necessary for the adhesion. Alternatively, when the content of a water-soluble reducing compound dissolved in a conventional aqueous curable composition is reduced for securing the time necessary for the adhesion, it is difficult to attain a sufficient adhesive property against a wetting material and particularly a biological hard tissue such as a dentine including a large amount of oxygen. On the contrary, the powdered water-soluble reducing compound (c) of the present composition existing on an adhesion interface is dissolved in water on the surface of a wetting material. There is a high frequency of encounter in a molecular state between the powdered water-soluble reducing compound (c) dissolved in the water and the organic peroxide (b) dissolved in the liquid radical polymeric monomer (a). In other words, a redox reaction, that is, a radical formation reaction, is easily proceeded. On the other hand, the powdered water-soluble reducing compound (c) existing within the present composition is in the form of a powder (solid) that is not dissolved in the liquid radical polymeric monomer (a) and hence there is a low frequency of encounter in a molecular state with the organic peroxide (b) dissolved in the liquid radical polymeric monomer (a). As a result, merely the polymeric curing property attained on the adhesion interface necessary to improve is selectively improved. This is the reason whey the present composition exhibits high adhesive strength against a wetting material. Also, the curing time of the present composition is longer than that of a conventional aqueous curable composition in which the same kind of powdered water-soluble reducing compound (c) is included in the same content not in a dispersed state but in a dissolved state for the following reason: The powdered water-soluble reducing compound (c) existing within the present composition is in a powder (solid) state and hence there is a low frequency of encounter in a molecular state with the organic peroxide (b), and therefore, the polymeric curing speed of the whole composition is not very high.

BEST MODE FOR CARRYING OUT INVENTION

The liquid radical polymeric monomer (a) is a polymeric monomer that is polymerized through a radical polymerization reaction proceeded by a redox polymerization initiator. It is noted that "liquid" herein means being in a liquid state at room temperature (25° C.). The number of kinds of radical polymeric monomers included in the liquid radical polymeric monomer (a) of this invention is not limited to one but may be two or more, and the whole radical polymeric monomers to be used should be in the form of liquid at room temperature. Specifically, in the case where the liquid radical polymeric monomer (a) includes merely one kind of radical polymeric monomer, the radical polymeric monomer should be in the form of liquid at room temperature. Alternatively, in the case where the liquid radical polymeric monomer (a) includes two or more kinds of radical polymeric monomers, the mixture thereof should be in the form of liquid at room temperature. Accordingly, in the case where the liquid radical polymeric monomer (a) includes a combination of two or more kinds of radical polymeric monomers, radical polymeric monomers in the form of liquid at room temperature may be combined with each other or radical polymeric monomers respectively in the form of liquid and solid at room temperature may be combined with each other as far as a mixture obtained from the combination is in the form of liquid at room temperature. Examples of radical polymeric monomers that can be included in the liquid radical polymeric monomer (a) are esters of carboxylic acids such as α-cyanoacrylic acid, (meth) acrylic acid, α-halogenated acrylate, crotonic acid, cinnamic acid, sorbic acid, maleic acid and itaconic acid, (meth)acrylamide and a derivative thereof, vinyl esters, vinyl ethers, a mono-N-vinyl derivative and a styrene derivative. Among them, (meth)acrylic acid ester is preferred.

Specific examples of the radical polymeric monomers that can be included in the liquid radical polymeric monomer (a) are as follows, in which a monomer having one olefin double bond is designated as a monofunctional monomer, a monomer having two olefin double bonds is designated as a bifunctional monomer and a monomer having three or more olefin double bonds is designated as a tri- or multi functional monomer:

Monofunctional Monomers:
methyl (meth)acrylate, ethyl (meth)acrylate, propyl (meth) acrylate, isopropyl (meth)acrylate, butyl (meth)acrylate, isobutyl (meth)acrylate, benzyl (meth)acrylate, lauryl (meth) acrylate, 2,3-dibromopropyl (meth)acrylate, 2-hydroxyethyl (meth)acrylate, 2-hydroxypropyl (meth)acrylate, 3-hydroxypropyl (meth)acrylate, 1,3-dihydroxypropyl (meth)acrylate, 2,3-dihydroxypropyl (meth)acrylate, 2-hydroxyethyl (meth) acrylamide, 3-methacryloyloxypropyl trimethoxysilane, 11-methacryloyloxyundecyl trimethoxysilane, (meth)acrylamide Bifunctional Monomers:

ethylene glycol di(meth)acrylate, triethylene glycol di(meth)acrylate, propylene glycol di(meth)acrylate, polyethylene glycol di(meth)acrylate (having nine or more oxyethylene groups), neopentyl glycol di(meth)acrylate, 1,6-hexanediol di(meth)acrylate, 1,10-decanediol di(meth)acrylate, dipentaerythritol di(meth)acrylate, bisphenol A diglycidyl (meth)acrylate, 2,2-bis[4-(meth)acryloyloxyethoxyphenyl]propane, 2,2-bis[4-(meth)acryloyloxypolyethoxyphenyl]propane, 2,2-bis[4-[3-(meth)acryloyloxy-2-hydroxypropoxy]phenyl]propane, 1,2-bis[3-(meth) acryloyloxy-2-hydropropoxy]ethane, pentaerythritol di(meth)acrylate, 1,2-bis(3-methacryloyloxy-2-hydroxypropoxy)ethane, [2,2,4-trimethylhexamethylene bis(2-carbamoyloxyethyl)]dimethacrylate, 1,3-di(meth)acryloyloxy-2-hydroxypropane Tri- or Multi Functional Monomers:

trimethylolpropane tri(meth)acrylate, trimethylolethane tri(meth)acrylate, tetramethylolmethane tri(meth)acrylate, pentaerythritol tetra(meth)acrylate, N,N'-(2,2,4-trimethylhexamethylene) bis[2-(aminocarboxy)propane-1,3-diol]tetramethacrylate, 1,7-diacryloyloxy-2,2,6,6-tetraacryloyloxymethyl-4-oxyheptane In order to improve the adhesive property against a wetting material, an acidic group-containing polymeric monomer that improves the affinity with the wetting material and has a decalcification function is preferably included as a part of the radical polymeric monomer that can be included in the liquid radical polymeric monomer (a). An example of the acidic group-containing polymeric monomer is a polymeric monomer having at least one acidic group such as a phosphoric acid group, a pyrophosphoric acid group, a carboxylic acid group or a sulfonic acid group, and at least one polymeric group (a polymerizable unsaturated group) such as an acryloyl group, a methacryloyl group, a vinyl group or a styrene group. Specific examples of such a polymeric monomer are as follows:

Examples of a phosphoric acid group-containing polymeric monomer are 2-(meth)acryloyloxyethyl dihydrogenphosphate, 3-(meth)acryloyloxypropyl dihydrogenphosphate, 4-(meth)acryloyloxybutyl dihydrogenphosphate, 5-(meth)acryloyloxypentyl dihydrogenphosphate, 6-(meth)acryloyloxyhexyl dihydrogenphosphate, 7-(meth)acryloyloxyheptyl dihydrogenphosphate, 8-(meth)acryloyloxyoctyl dihydrogenphosphate, 9-(meth)acryloyloxynonyl dihydrogenphosphate, 10-(meth)acryloyloxydecyl dihydrogenphosphate, 11-(meth)acryloyloxyundecyl dihydrogenphosphate, 12-(meth)acryloyloxydodecyl dihydrogenphosphate, 16-(meth)acryloyloxyhexadecyl dihydrogenphosphate, 20-(meth)acryloyloxyeicosyl dihydrogenphosphate, bis[2-(meth)acryloyloxyethyl]hydrogenphosphate, bis[4-(meth) acryloyloxybutyl]hydrogenphosphate, bis[6-(meth) acryloyloxyhexyl]hydrogenphosphate, bis[8-(meth) acryloyloxyoctyl]hydrogenphosphate, bis[9-(meth) acryloyloxynonyl]hydrogenphosphate, bis[10-(meth) acryloyloxydecyl]hydrogenphosphate, 1,3-di(meth) acryloyloxypropyl-2-dihydrogenphosphate, 2-(meth) acryloyloxyethylphenyl hydrogenphosphate, 2-(meth) acryloyloxyethyl 2'-bromoethyl hydrogenphosphate, 2-(meth)acryloyloxyethyl-phenylphosphonate; (5-methacryloxy)pentyl-3-phosphonopropyonate, (6-methacryloxy) hexyl-3-phosphonopropyonate, (10-methacryloxy)decyl-3-phosphonopropionate, (6-methacryloxy)hexyl-3-phosphonoacetate, (10-methacryloxy)decyl-3-phosphonoacetate, 2-methacryloyloxyethyl (4-methoxyphenyl)hydrogenphosphate, 2-methacryloyloxypropyl (4-methoxyphenyl)hydrogenphosphate, phosphoric acid group-containing polymeric monomers and their acid chlorides described in Japanese Laid-Open Patent Publication No. Sho 52-113089, Japanese Laid-Open Patent Publication No. Sho 53-67740, Japanese Laid-Open Patent Publication No. Sho 53-69494, Japanese Laid-Open Patent Publication No. Sho 53-144939, Japanese Laid-Open Patent Publication No. Sho 58-128393 and Japanese Laid-Open Patent Publication No. Sho 58-192891.

Examples of a pyrophosphoric acid group-containing polymeric monomer are bis[2-(meth)acryloyloxyethyl]pyrophosphate, bis[4-(meth)acryloyloxybutyl]pyrophosphate, bis[6-(meth)acryloyloxyhexyl]pyrophosphate, bis[8-(meth) acryloyloxyoctyl]pyrophosphate, bis[10-(meth)acryloyloxydecyl]pyrophosphate and their acid chlorides.

Examples of a carboxylic acid group-containing polymeric monomer are maleic acid, methacrylic acid, 4-(meth)acryloyloxyethoxycarbonylphthalic acid, 4-(meth)acryloyloxybutyloxycarbonylphthalic acid, 4-(meth)acryloyloxyhexyloxycarbonylphthalic acid, 4-(meth) acryloyloxyoctyloxycarbonylphthalic acid, 4-(meth) acryloyloxydecyloxycarbonylphthalic acid and their acid anhydrides, 5-(meth)acryloylaminopentylcarboxylic acid, 6-(meth)acryloyloxy-1,1-hexanedicarboxylic acid, 8-(meth) acryloyloxy-1,1-octanedicarboxylic acid, 10-(meth)acryloyloxy-1,1-decanedicarboxylic acid, 11-(meth)acryloyloxy-1,1-undecanedicarboxylic acid and their acid chlorides.

Examples of a sulfonic acid group-containing polymeric monomer are 2-(meth)acrylamide-2-methylpropane sulfonate, styrene sulfonic acid and 2-sulfoethyl (meth)acrylate. In particular, in the case where a polymeric monomer including a phosphoric acid group or a thiophosphoric acid group represented by Chemical Formula 1 below or, more preferably, including a phosphoric acid group or a thiophosphoric acid group represented by Chemical Formula 2 or 3 below is used, a curable composition exhibiting a high adhesive property against a wetting material and a dentine in particular is obtained.

Chemical Formula 1

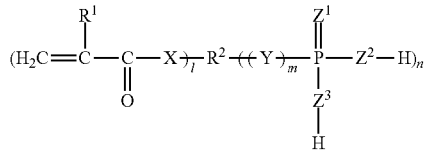

[wherein $R^1$ is hydrogen or a methyl group, $R^2$ is a (1+n)-valent group with a carbon number of 2 through 40, l is an integer of 1 through 5, m is 0 or 1, n is an integer of 1 through 4, —X— is —O— or —NH—, —Y— is —O— or —S—, and $Z^1$, $Z^2$ and $Z^3$ are independently an oxygen atom or a sulfur atom.]

Chemical Formula 2

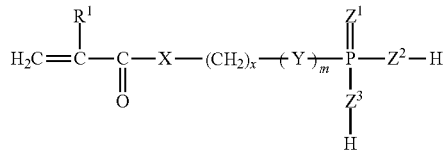

[wherein R$^1$ is hydrogen or a methyl group, x is an integer of 4 through 20, m is 0 or 1, —X— is —O— or —NH—, —Y— is —O— or —S—, and Z$^1$, Z$^2$ and Z$^3$ are independently an oxygen atom or a sulfur atom.]

Chemical Formula 3

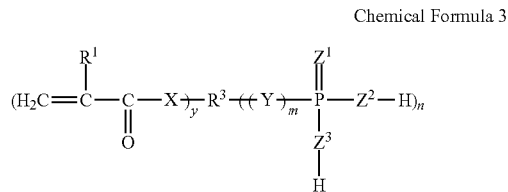

[wherein R$^1$ is hydrogen or a methyl group, R$^3$ is a (y+n)-valent group with a carbon number of 3 through 10, y is an integer of 2 through 5, m is 0 or 1, n is an integer of 1 through 4, —X— is —O— or —NH—, —Y— is —O— or —S—, and Z$^1$, Z$^2$ and Z$^3$ are independently an oxygen atom or a sulfur atom.]

One of or a combination of two or more of the exemplified radical polymeric monomers is used as far as the liquid radical polymeric monomer (a) can be constructed. It is herein noted that a word "(meth)acryl" is generically used for "acryl" and "methacryl", that a word "(meth)acrylate" is generically used for "acrylate" and "methacrylate", and that a word "(meth)acryloyl" is generically used for "acryloyl" and "methacryloyl".

The organic peroxide (b) is an oxidant component of the redox polymerization initiator. Examples of the organic peroxide (b) are diacyl peroxides, peroxy esters, dialkyl peroxides, peroxy ketals, ketone peroxides and hydroperoxides. Specific examples of the diacyl peroxides are benzoyl peroxide, 2,4-dichlorobenzoyl peroxide and m-toluoyl peroxide. Specific examples of the peroxy esters are t-butyl peroxybenzoate, bis-t-butyl peroxyisophthalate, 2,5-dimethyl-2,5-bis (benzoylperoxy)hexane, t-butyl peroxy-2-ethyl hexanoate and t-butyl peroxyisopropyl carbonate. Specific examples of the dialkyl peroxides are dicumyl peroxide, di-t-butyl peroxide and lauroyl peroxide. Specific examples of the peroxy ketals are 1,1-bis(t-butyl peroxy)3,3,5-trimethyl cyclohexane, 1,1-bis(t-butyl peroxy)cyclohexane and 1,1-bis(t-hexyl peroxy)cyclohexane. Specific examples of the ketone peroxides are methyl ethyl ketone peroxide, cyclohexanone peroxide and methyl acetoacetate peroxide. Specific examples of the hydroperoxides are t-butyl hydroperoxide, cumene hydroperoxide and p-diisopropyl benzene peroxide.

The powdered water-soluble reducing compound (c) is a reductant component of the redox polymerization initiator. As described above, the most remarkable characteristic of this invention is that the powdered water-soluble reducing compound (c) is not dissolved in an aqueous curable composition but dispersed in a nonaqueous curable composition. A word "nonaqueous" herein means that water is not positively included and does not mean that even a slight amount of moisture unavoidably mixed is excluded. Also, a word "water-soluble" herein means solubility in water at room temperature (25° C.) of 0.5 mg/100 mL or more. The powdered water-soluble reducing compound (c) preferably has the solubility of 1 mg/100 mL or more. Examples of the powdered water-soluble reducing compound (c) are powders of sulfite, hydrogensulfite, pyrosulfite, thiosulfite, thionate and dithionite. Among these examples, the powder of sulfite or hydrogensulfite is preferred because of the low solubility in the liquid radial polymeric monomer (a), high water-solubility, high performance as a reductant and so on, and in particular, the powder of sulfite such as sodium sulfite, potassium sulfite, calcium sulfite, ammonium sulfite, sodium hydrogensulfite, or potassium hydrogensulfite is the most preferred. The dispersed state of the powdered water-soluble reducing compound (c) in the present composition can be confirmed by curing the present composition in an environment including no water, breaking the thus cured composition and observing the broken surface with an energy dispersive micro X-ray fluorescence spectrometer.

The average particle diameter of the powdered water-soluble reducing compound (c) is not particularly specified, and is preferably 500 µm or less and more preferably 100 µm or less because the powder is easily precipitated when it is too large. On the other hand, the average particle diameter is preferably 0.01 µm or more because when it is too small, the specific surface area of the powder is too large and the amount that can be dispersed in the liquid radical polymeric monomer (a) is reduced. In other words, the average particle diameter of the powdered water-soluble reducing compound (c) is preferably 0.01 through 500 µm and more preferably 0.01 through 100 µm.

The shape of the powdered water-soluble reducing compound (c) is not particularly specified and may be any of various shapes including a spherical shape, a needle shape, a plate shape and a crushed shape. The powdered water-soluble reducing compound (c) can be produced by any of known methods such as a grinding method and a freeze-dry method.

Preferable ratios of the organic peroxide (b) and the powdered water-soluble reducing compound (c) based on 100 parts by weight of the liquid radical polymeric monomer (a) are respectively 0.05 through 10 parts by weight (more preferably 0.1 through 5 parts by weight) and 0.01 through 15 parts by weight (more preferably 0.05 through 10 parts by weight).

In the case where the acidic group-containing polymeric monomer is used as a part of the liquid radical polymeric monomer (a), the ratio of the acidic group-containing polymeric monomer based on 100 parts by weight of the liquid radical polymeric monomer (a) excluding the acidic group-containing polymeric monomer is preferably 1 through 200 parts by weight (more preferably 5 through 150 parts by weight).

In order to adjust a curing time of the present composition, known aromatic secondary amine, aromatic tertiary amine, aromatic sulfinate or the like may be used, together with the powdered water-soluble reducing compound (c), as a reductant component of the redox polymerization initiator. However, attention has to be paid to the content of such an arbitrary reductant component because the work time may be largely reduced when the content is too large.

Examples of the aromatic secondary amine or the aromatic tertiary amine are N-methylaniline, N-methyl-p-toluidine, N-methyl-m-toluidine, N-methyl-o-toluidine, N-ethanol-p-toluidine, N-ethanol-m-toluidine, N-ethanol-o-toluidine, ethyl p-methylaminobenzoate, ethyl m-methylaminobenzoate, ethyl o-methylaminobenzoate, p-methyl amino anisole, m-methyl amino anisole, o-methyl amino anisole, 1-methyl amino naphthalene, 2-methyl amino naphthalene, N,N-dimethylaniline, N,N-dimethyl-p-toluidine, N,N-dimethyl-m-toluidine, N,N-dimethyl-o-toluidine, N,N-diethanol-p-toluidine, N,N-diethanol-m-toluidine, N,N-diethanol-o-toluidine, ethyl p-dimethylaminobenzoate, ethyl m-dimethylaminobenzoate, ethyl o-dimethylaminobenzoate, p-dimethylaminoanisole, m-dimethylaminoanisole, o-dimethylaminoanisole, 1-dimethylaminonaphthalene and 2-dimethylaminonaphthalene. The ratio of the aromatic secondary amine or the aromatic tertiary amine based on 100 parts by weight of the liquid radical polymeric monomer (a) is preferably 0.01 through 10 parts by weight (more preferably 0.03 through 5 parts by weight).

Examples of the aromatic sulfinate are lithium salts, sodium salts, potassium salts, rubidium salts, cesium salts, magnesium salts, calcium salts, strontium salts, iron salts, copper salts, zinc salts, ammonium salts, tetramethyl ammonium salts and tetraethyl ammonium salts of benzene sulfonic acid, p-toluene sulfonic acid, o-toluene sulfonic acid, ethyl benzene sulfonic acid, decyl benzene sulfonic acid, dodecyl benzene sulfonic acid, 2,4,6-trimethyl benzene sulfonic acid, 2,4,6-triisopropyl benzene sulfonic acid, chlorobenzene sulfonic acid, naphthalene sulfonic acid or the like. The ratio of the aromatic sulfinate based on 100 parts by weight of the liquid radical polymeric monomer (a) is preferably 0.01 through 10 parts by weight (more preferably 0.03 through 5 parts by weight).

In order to improve the mechanical strength attained after curing, the present composition may include a glass filler. The glass filler to be included may be an ion unexchangeable glass filler or an ion exchangeable glass filler, or both of them may be used together. Examples of the ion unexchangeable glass filler are an inorganic filler, an organic filler and a complex filler of an inorganic filler and an organic filler. Examples of the inorganic filler are silica; a mineral including silica as a matrix and further including kaoline, clay, isinglass or mica; ceramics including silica as a matrix and further including $Al_2O_3$, $B_2O_3$, $TiO_2$, $ZrO_2$, BaO, $La_2O_3$, $SrO_2$, CaO, $P_2O_5$ or the like; and glass such as lanthanum glass, barium glass or strontium glass. Furthermore, crystalline quartz, hydroxyapatite, alumina, titanium oxide, ytterbium oxide, ytterbium fluoride, zirconia, barium sulfate or the like may be also used as the inorganic filler. Examples of the organic filler are organic resins such as polymethyl methacrylate, polyamide, polystyrene, polyvinyl chloride, chloroprene rubber, nitrile rubber and styrene-butadiene rubber. Examples of the complex filler are a filler obtained by dispersing a ion unexchangeable glass filler in any of the above-described organic resins and a non-eluting filler coated with any of the above-described organic resins. An example of the ion exchangeable glass filler is fluoroalumino silicate glass (such as calcium fluoroalumino silicate glass, strontium fluoroalumino silicate glass or barium fluoroalumino silicate glass) including an exchangeable cation having a valence of 2 or more and reactive with an acidic group-containing polymeric monomer (such as strontium, calcium, zinc, aluminum, iron or zirconium). Such a filler may be used after a surface treatment with a known surface-treatment agent such as a silane coupling agent if necessary. Examples of the surface-treatment agent are vinyltrimethoxysilane, vinyltriethoxysilane, vinyltrichlorosilane, vinyltri(β-methoxyethoxy)silane, γmethacryloyloxypropyltrimethoxysilane, γglycidoxypropyltrimethoxysilane, γmercaptopropyltrimethoxysilane and γaminopropyltriethoxysilane.

In the case where the application target is a biological hard tissue and more particularly a tooth, the present composition may include a known water-soluble fluoride compound for releasing fluorine ions in a content not to lower the adhesive property. Examples of the water-soluble fluoride compound are lithium fluoride, sodium fluoride, potassium fluoride, rubidium fluoride, cesium fluoride, beryllium fluoride, magnesium fluoride, calcium fluoride, strontium fluoride, barium fluoride, zinc fluoride, aluminum fluoride, manganese fluoride, copper fluoride, lead fluoride, silver fluoride, antimony fluoride, cobalt fluoride, bismuth fluoride, tin fluoride, diamine silver fluoride, sodium monofluorophosphate, titanium potassium fluoride, stannate fluoride and fluorosilicate.

One of these water-soluble fluoride compounds may be singly used or a plurality of them may be mixedly used. In the case where the water-soluble fluoride compound is used, it is preferably shaped into fine particles by a method described in Japanese Laid-Open Patent Publication No. Sho 2-258602 or the like, or coated with polysiloxane by a method described in Japanese Laid-Open Patent Publication No. Hei 10-36116 before adding it to the composition.

The present composition may include any of known stabilizers, photopolymerization initiators, dyes and pigments.

As a packing form for the present composition, a divided packing form is preferably employed from the viewpoint of storage stability. As the divided packing form, the present composition is preferably divided into two packs of a first agent including the liquid radical polymeric monomer (a) and the organic peroxide (b) and a second agent including the liquid radical polymeric monomer (a) and the powdered water-soluble reducing compound (c). In the case where an acidic group-containing polymeric monomer is included in the present composition, the present composition is preferably divided into two packs of a first agent including the liquid radical polymeric monomer (a) containing the acidic group-containing polymeric monomer and the organic peroxide (b) and a second agent including the liquid radical polymeric monomer (a) not containing the acidic group-containing polymeric monomer and the powdered water-soluble reducing compound (c). When the acidic group-containing polymeric monomer is used, it is included in the first agent for the following reason: If it is included in the second agent, the powdered water-soluble reducing compound (c) such as an alkali metal salt is decomposed through a reaction with the acidic group-containing polymeric monomer during storage, which may reduce the amount of radicals to be formed.

In the case where the present composition is dividedly packed as the first agent including the liquid radical polymeric monomer (a) and the organic peroxide (b) and the second agent including the liquid radical polymeric monomer (a) and the powdered water-soluble reducing compound (c), the first agent is prepared by mixing 0.1 through 50 parts by weight of the organic peroxide (b) in 100 parts by weight of the liquid radical polymeric monomer (a), the second agent is prepared by mixing 0.1 through 50 parts by weight of the powdered water-soluble reducing compound (c) in 100 parts by weight of the liquid radical polymeric monomer (a), and the first agent and the second agent are mixed in a weight ratio of 1:10 through 10:1 for use.

When the packing form is the divided packing form composed of the first agent and the second agent, the first agent and the second agent are mixed to obtain one mixed agent before use, and the mixed agent is applied on a wetting material. The curing reaction speed is accelerated on an adhesion interface through contact between the mixed agent and a water content present on the wetting material, and when the curing reaction is completed, the present composition is adhered onto the wetting material. This will be described by exemplifying application to a tooth. When a cavity of a tooth is filled for treatment, the tooth cavity is cleaned by a general method, and the mixed agent of the present composition is filled in the tooth cavity. When a prosthesis material such as a crown or an inlay is adhered to an abutment tooth or a tooth cavity, an adhesion surface of the abutment tooth or the tooth cavity and an adhesion surface of the prosthesis material are cleaned, and the mixed agent of the present composition is applied onto at least one of the adhesion surface of the abutment tooth or the tooth cavity and the adhesion surface of the prosthesis material for adhesion. Before applying the present composition onto a tooth surface, the tooth surface may be subjected to a known pretreatment such as an etching treatment with an acidic aqueous solution, a reforming treatment with a primer, or an etching/reforming treatment with a primer having an etching function.

Embodiments

The present invention will now be described in detail on the basis of preferred embodiments thereof, and it is noted that the invention is not limited to the following embodiments. Abbreviations used in description below stand for the following:

Bis-GMA: 2,2-bis[4-(3-methacryloyloxy-2-hydroxypropoxy)phenyl]propane
TEGDMA: triethylene glycol dimethacrylate
NPG: neopentyl glycol dimethacrylate
HEMA: 2-hydroxyethyl methacrylate
MDP: 10-methacryloyloxydecyl dihydrogenphosphate
BPO: benzoyl peroxide
DEPT: N,N-diethanol-p-toluidine
TPBSS: sodium 2,4,6-triisopropyl benzene sulfinate (Embodiment 1)

Agents A1-1 and A1-2 having compositions described below were prepared and combined, so as to produce a divided type nonaqueous curable composition (present composition) including these agents in a weight ratio of 1:1. In the composition obtained by mixing the agents A1-1 and A1-2, sodium sulfite was in a dispersed state. The divided type nonaqueous curable composition was subjected to a curing time test (P1) and a tensile bond strength test (Q1) described below, so as to obtain a curing time and tensile bond strength. The results are listed in Table 1 below. It is noted that the average particle diameter of a powdered water-soluble reducing compound (that is, a sodium sulfite powder in Embodiment 1) was measured by using ethanol as a dispersing medium with a laser diffraction particle size analyzer SALD-2100 (manufactured by Shimadzu Corporation) (which measurement method was similarly employed in other embodiments below).

Agent A1-1:

| Bis-GMA | 40 parts by weight |
| HEMA | 20 parts by weight |
| TEGDMA | 20 parts by weight |
| MDP | 20 parts by weight |
| BPO | 1 part by weight |

Agent A1-2:

| Bis-GMA | 40 parts by weight |
| HEMA | 40 parts by weight |
| TEGDMA | 20 parts by weight |
| Sodium sulfite powder (with an average particle diameter of 6.1 μm) | 3 parts by weight |

[Curing Time Test (P1)]

The agents A1-1 and A1-2 were placed, in an amount of 0.1 g each, in a hemispherical plastic vessel with a diameter of 1 cm and a depth of 5 mm to be well mixed with a spatula, so as to obtain a mixed agent. Immediately after the mixing, a thermocouple (manufactured by Okazaki Manufacturing Company) connected to a recorder (manufactured by Yokogawa Electric Corporation) was inserted into the mixed agent, so as to record temperature change caused in a polymeric curing reaction with the recorder, and a curing time (time elapsed from the mixing to a rise of an exothermic peak) was thus obtained.

[Tensile Bond Strength Test (Q1)]

The labial surface of a lower anterior tooth of a bovine was polished with #80 silicon carbide paper (manufactured by Nihon Kenshi Co., Ltd.) in running water so as to form two kinds of flat surfaces of an enamel and a dentine. Each flat surface was further polished with #1000 silicon carbide paper (manufactured by Nihon Kenshi Co., Ltd.) in running water so as to form a smooth surface. An adhesive tape with a thickness of approximately 150 μm having a hole with a diameter of 4 mm was adhered onto the smooth surface for restricting an adhesion area. Subsequently, the mixture of the agents A1-1 and A1-2 was applied within the hole with a small brush. The mixture was applied in a thickness of approximately 100 μm. Then, a commercially available photopolymerizable dental composite resin (manufactured by Kuraray Medical Inc., trade name "Clearfil AP-X") was placed on the applied surface, and the resultant was irradiated for curing with a dental visible light irradiator (manufactured by J. Morita USA, trade name "JETLITE 3000") for 40 seconds. One end of a cylindrical bar of SUS304 with a size of 7 mmφ×25 mm was adhered on the thus obtained cured substance with a commercially available dental resin cement (Manufactured by Kuraray Medical Inc., trade name "Panavia fluorocement"), thereby obtaining a test piece. One hour after the adhesion, the test piece was immersed in water of a temperature of 37° C. and was taken out of the water after 24 hours, and tensile bond strength was measured with a universal testing machine (manufactured by Shimadzu Corporation). The tensile bond strength was measured with a cross head speed set to 2 mm/min. An average of measured values obtained in eight test pieces was regarded as the tensile bond strength of the test pieces.

(Embodiment 2)

An agent A2-2 having a composition described below was prepared by replacing 3 parts by weight of a sodium sulfite powder of the agent A1-2 of Embodiment 1 with 2 parts by weight of a potassium sulfite powder, and the agent A2-2 was combined with the agent A1-1 of Embodiment 1, so as to produce a divided type nonaqueous curable composition (present composition) including these agents in a weight ratio of 1:1. In the composition obtained by mixing the agents A2-2 and A1-1, potassium sulfite was in a dispersed state. This divided type nonaqueous curable composition was subjected to the aforementioned curing time test (P1) and tensile bond strength test (Q1) so as to obtain a curing time and tensile bond strength. The results are listed in Table 1 below.

Agent A2-2:

| Bis-GMA | 40 parts by weight |
| HEMA | 40 parts by weight |
| TEGDMA | 20 parts by weight |
| Potassium sulfite powder (with an average particle diameter of 9.9 μm) | 2 parts by weight |

COMPARATIVE EXAMPLE 1

An agent A3-2 having a composition described below was prepared by adding 10 parts by weight of water to the agent A1-2 of Embodiment 1, and the agent A3-2 was combined with the agent A1-1 of Embodiment 1, so as to produce a divided type aqueous curable composition including these agents in a weight ratio of 1:1. In the composition obtained by mixing the agents A3-2 and A1-1, sodium sulfite was in a dissolved state. This divided type aqueous curable composition was subjected to the aforementioned curing time test (P1) and tensile bond strength test (Q1) so as to obtain a curing time and tensile bond strength. The results are listed in Table 1 below.

Agent A3-2:

| | |
|---|---|
| Bis-GMA | 40 parts by weight |
| HEMA | 40 parts by weight |
| TEGDMA | 20 parts by weight |
| water | 10 parts by weight |
| Sodium sulfite powder (with an average particle diameter of 6.1 μm) | 3 parts by weight |

COMPARATIVE EXAMPLE 2

An agent A4-2 having a composition described below was prepared by changing the content of sodium sulfite powder of the agent A3-2 of Comparative Example 1 from 3 parts by weight to 0.1 part by weight, and this agent A4-2 was combined with the agent A1-1 of Embodiment 1, so as to produce a divided type aqueous curable composition including these agents in a weight ratio of 1:1. In the composition obtained by mixing the agents A4-2 and A1-1, sodium sulfite was in a dissolved state. This divided type aqueous curable composition was subjected to the aforementioned curing time test (P1) and tensile bond strength test (Q1) so as to obtain a curing time and tensile bond strength. The results are listed in Table 1 below.

Agent A4-2:

| | |
|---|---|
| Bis-GMA | 40 parts by weight |
| HEMA | 40 parts by weight |
| TEGDMA | 20 parts by weight |
| water | 10 parts by weight |
| Sodium sulfite powder (with an average particle diameter of 6.1 μm) | 0.1 part by weight |

TABLE 1

| | | Embodiment 1 | Embodiment 2 | Comparative Example 1 | Comparative Example 2 |
|---|---|---|---|---|---|
| Curing Time | | 5 min. 30 sec. | 5 min. 10 sec. | Cured during mixing | 5 min. 30 sec. |
| Tensile Bond Strength (MPa) | Enamel | 18.3 | 17.6 | — | 15.3 |
| | Dentine | 12.0 | 13.2 | — | 5.1 |

As shown in Table 1, the present compositions produced in Embodiments 1 and 2 were not largely reduced in the curing time as the whole compositions. This seems to be because each of these compounds included a large amount of water-soluble reducing compound but did not include water, and hence, the amount of radicals formed within the composition was not largely increased. Also, on the adhesion interface of each of the present compositions produced in Embodiments 1 and 2, the polymeric curing reaction was rapidly proceeded so as to exhibit high adhesive strength. This seems to be because the composition could form radicals in a large amount sufficient for suppressing the polymerization inhibition caused by oxygen on the adhesion interface where water is present. On the other hand, the aqueous curable composition produced in Comparative Example 1 was cured during the mixing, and the aqueous curable composition produced in Comparative Example 2 was poor at the adhesive strength against a dentine. The curing time of the aqueous curable composition produced in Comparative Example 1 was very short probably because the sodium sulfite was in a dissolved state and hence a redox reaction with BPO (benzoyl peroxide) was rapidly proceeded after the mixing. The adhesive strength against a dentine of the aqueous curable composition produced in Comparative Example 2 was low probably for the following reason: Since the content of the sodium sulfite powder was reduced for attaining a practical work time of the curable composition, radicals were not formed in an amount sufficient for suppressing the polymerization inhibition caused by oxygen on the adhesion interface.

(Embodiment 3)

Agents B1-1 and B1-2 having compositions described below were prepared and combined, so as to produce a divided type nonaqueous curable composition (present composition) including these agents in a weight ratio of 1:1. In the composition obtained by mixing the agents B1-1 and B1-2, sodium sulfite was in a dispersed state. This divided type nonaqueous curable composition was subjected to the aforementioned curing time test (P1) for obtaining a curing time and was also subjected to a tensile bond strength test (Q2) described below for obtaining tensile bond strength. The results are listed in Table 2 below.

Agent B1-1:

| | |
|---|---|
| Bis-GMA | 40 parts by weight |
| HEMA | 30 parts by weight |
| NPG | 30 parts by weight |
| BPO | 1 part by weight |

Agent B1-2:

| | |
|---|---|
| Bis-GMA | 40 parts by weight |
| HEMA | 30 parts by weight |
| NPG | 30 parts by weight |
| Sodium sulfite powder (with an average particle diameter of 6.1 μm) | 1 part by weight |

[Tensile Bond Strength Test (Q2)]

The labial surface of a lower anterior tooth of a bovine was polished with #80 silicon carbide paper (manufactured by Nihon Kenshi Co., Ltd.) in running water so as to form two kinds of flat surfaces of an enamel and a dentine. Each of the flat surfaces was further polished with #1000 silicon carbide paper (manufactured by Nihon Kenshi Co., Ltd.) in running water so as to form a smooth surface. An adhesive tape with a thickness of approximately 150 μm having a hole with a diameter of 4 mm was adhered onto the smooth surface for restricting an adhesion area. Subsequently, a primer composition including 65 parts by weight of water, 25 parts by weight of HEMA and 10 parts by weight of MDP was applied within the hole with a brush, and the resultant was allowed to stand for 30 seconds and then dried with an air syringe until the primer composition lost its flowability. Thereafter, the mixture of the agents B1-1 and B1-2 was applied with a small brush on the surface where the primer composition had been applied. The mixture was applied in a thickness of approximately 100 μm. Then, a commercially available photopolymerizable dental composite resin (the aforementioned "Clearfil AP-X") was placed on the applied surface, and the resultant was irradiated for curing with a dental visible light irradiator (the aforementioned "JETLITE 3000") for 40 seconds. One end of a cylindrical bar of SUS304 with a size of 7 mmϕ×25 mm was adhered on the thus obtained cured substance with a commercially available dental resin cement (the aforementioned "Panavia fluorocement"), thereby obtaining a test piece. One hour after the adhesion, the test piece was immersed in water of a temperature of 37° C. and was taken out of the water after 24 hours, and tensile bond strength was measured with a universal testing machine (manufactured by Shimadzu Corporation). The tensile bond strength was measured with a cross head speed set to 2 mm/min. An average of measured values obtained in eight test pieces was regarded as the tensile bond strength of the test pieces.

(Embodiment 4)

An agent B2-2 having a composition described below was prepared, and the agent B2-2 was combined with the agent B1-1 of Embodiment 3, so as to produce a divided type nonaqueous curable composition (present composition) including these agents in a weight ratio of 1:1. In the agent B2-2 and in the composition obtained by mixing the agents B1-1 and B2-2, sodium sulfite was in a dispersed state. This divided type nonaqueous curable composition was subjected to the aforementioned curing time test (P1) and tensile bond strength test (Q2) so as to obtain a curing time and tensile bond strength. The results are listed in Table 2 below.

Agent B2-2:

| | |
|---|---|
| Bis-GMA | 40 parts by weight |
| HEMA | 40 parts by weight |
| NPG | 20 parts by weight |
| Sodium sulfite powder (with an average particle diameter of 8.1 μm) | 2 parts by weight |

COMPARATIVE EXAMPLE 3

An agent B3-2 having a composition described below was prepared, and the agent B3-2 was combined with the agent B1-1 of Embodiment 3, so as to produce a divided type nonaqueous curable composition including these agents in a weight ratio of 1:1. This divided type nonaqueous curable composition was subjected to the aforementioned curing time test (P1) and tensile bond strength test (Q2) so as to obtain a curing time and tensile bond strength. The results are listed in Table 2 below.

Agent B3-2:

| | |
|---|---|
| Bis-GMA | 40 parts by weight |
| HEMA | 40 parts by weight |
| NPG | 20 parts by weight |
| DEPT | 1 part by weight |

COMPARATIVE EXAMPLE 4

An agent B4-2 having a composition described below was prepared, and the agent B4-2 was combined with the agent B1-1 of Embodiment 3, so as to produce a divided type aqueous curable composition including these agents in a weight ratio of 1:1. In the composition obtained by mixing the agents B4-2 and B1-1, sodium sulfite was in a dissolved state. This divided type aqueous curable composition was subjected to the aforementioned curing time test (P1) and tensile bond strength test (Q2) so as to obtain a curing time and tensile bond strength. The results are listed in Table 2 below.

Agent B4-2:

| | |
|---|---|
| Bis-GMA | 40 parts by weight |
| HEMA | 40 parts by weight |
| NPG | 20 parts by weight |
| water | 10 parts by weight |
| Sodium sulfite powder (with an average particle diameter of 6.1 μm) | 0.1 part by weight |

TABLE 2

| | | Embodiment 3 | Embodiment 4 | Comparative Example 3 | Comparative Example 4 |
|---|---|---|---|---|---|
| Curing Time | | 3 min. 15 sec. | 3 min. 00 sec. | 2 min. 55 sec. | 2 min. 45 sec. |
| Tensile Bond Strength (MPa) | Enamel | 24.3 | 22.5 | 14.0 | 15.7 |
| | Dentine | 14.6 | 15.2 | 4.7 | 6.3 |

As shown in Table 2, the present compositions produced in Embodiments 3 and 4 had a practical curing time and exhibited high adhesive strength against both an enamel and a dentine. On the other hand, the nonaqueous curable composition produced in Comparative Example 3 and the aqueous curable composition produced in Comparative Example 4 both had low adhesive strength against a dentine. The adhesive strength against a dentine of the nonaqueous curable composition produced in Comparative Example 3 was low probably because the DEPT with a water-insoluble property was used as a reductant of the redox polymerization initiator and hence the aqueous curable composition was not sufficiently polymerically cured on the adhesion interface due to the polymerization inhibition caused by oxygen. The adhesive strength against a dentine of the aqueous curable composition produced in Comparative Example 4 was low probably because the content of sodium sulfite was largely reduced for attaining a practical work time and hence the aqueous curable composition was not sufficiently polymerically cured on the adhesion interface due to the polymerization inhibition caused by oxygen.

(Embodiments 5 Through 7 and Comparative Example 5)

Four kinds of divided type nonaqueous curable compositions having compositions listed in Table 3 (in each of which a weight ratio between two agents was 1:1) were produced. In the composition obtained by mixing a first agent and a second agent of each of the divided type nonaqueous curable compositions of Embodiments 5 through 7, a water-soluble reducing compound (sodium sulfite (with an average particle diameter of 6.1 μm) or potassium sulfite (with an average particle diameter of 12.3 μm)) was in a dispersed state. These divided type nonaqueous curable compositions were subjected to the aforementioned curing time test (P1) and tensile bond strength test (Q2) so as to obtain curing times and tensile bond strength. The results are listed in Table 4 below.

TABLE 3

| | | Composition (parts by weight) | | | |
|---|---|---|---|---|---|
| | | Embodiment 5 | Embodiment 6 | Embodiment 7 | Comparative Example 5 |
| First agent | Bis-GMA | 40 | 40 | 40 | 40 |
| | HEMA | 20 | 20 | 20 | 20 |
| | NPG | 20 | 20 | 20 | 20 |
| | MDP | 20 | 20 | 20 | 20 |
| | BPO | 1 | 1 | 1 | 1 |

TABLE 3-continued

| | | Composition (parts by weight) | | | |
|---|---|---|---|---|---|
| | | Embodiment 5 | Embodiment 6 | Embodiment 7 | Comparative Example 5 |
| Second agent | Bis-GMA | 40 | 40 | 40 | 40 |
| | HEMA | 40 | 40 | 40 | 40 |
| | NPG | 20 | 20 | 20 | 20 |
| | Sodium sulfite powder | 2 | 2 | — | — |
| | Potassium sulfite powder | — | — | 3 | — |
| | DEPT | 1 | 1 | 1 | 1 |
| | TPBSS | — | 1 | 1 | 1 |

TABLE 4

| | Embodiment 5 | Embodiment 6 | Embodiment 7 | Comparative Example 5 |
|---|---|---|---|---|
| Curing Time | 2 min. 30 sec. | 2 min. 10 sec. | 2 min. 50 sec. | 3 min. 15 sec. |
| Tensile Bond Strength (MPa) Enamel | 25.2 | 23.6 | 21.8 | 20.6 |
| Tensile Bond Strength (MPa) Dentine | 16.4 | 17.2 | 15.7 | 7.7 |

As shown in Table 4, the present compositions produced in Embodiments 5 through 7 had practical curing times and exhibited high adhesive strength against both an enamel and a dentine. On the other hand, the nonaqueous curable composition produced in Comparative Example 5 had low adhesive strength against a dentine. The adhesive strength against a dentine of the nonaqueous curable composition produced in Comparative Example 5 was low probably for the following reason: Since reducing compounds dissolving in the composition (DEPT and TPBSS) were used as reductants of the redox polymerization initiator, there was a high frequency of encounter in a molecular state between the organic peroxide and the reducing compounds in the composition, and hence, the amount of reducing compounds distributing the polymeric curing reaction on the adhesion interface was reduced. Therefore, the nonaqueous curable composition was not sufficiently polymerically cured on the adhesion interface.

(Embodiment 8)

Agents D1-1 and D1-2 having compositions described below were prepared and combined, so as to produce a divided type nonaqueous curable composition (present composition) including these agents in a weight ratio of 1:1. In the composition obtained by mixing the agents D1-1 and D1-2, sodium sulfite was in a dispersed state. This divided type nonaqueous curable composition was subjected to a curing time test (P2) described below for obtaining a curing time and was also subjected to a shear bond strength test (Q3) described below for obtaining shear bond strength. The results are listed in Table 5 below.

Agent D1-1:

| Bis-GMA | 40 parts by weight |
|---|---|
| HEMA | 20 parts by weight |
| TEGDMA | 20 parts by weight |
| MDP | 20 parts by weight |
| BPO | 1 part by weight |
| Silanated quartz filler | 300 parts by weight |

Agent D1-2:

| Bis-GMA | 40 parts by weight |
|---|---|
| HEMA | 40 parts by weight |
| TEGDMA | 20 parts by weight |
| Sodium sulfite powder (with an average particle diameter of 6.1 μm) | 2 parts by weight |
| DEPT | 1 part by weight |
| TPBSS | 1 part by weight |
| Silanated quartz filler | 300 parts by weight |

COMPARATIVE EXAMPLE 6

An agent D2-2 having a composition described below was prepared by excluding the sodium sulfite powder from the agent D1-2 of Embodiment 8, and the agent D2-2 was combined with the agent D1-1 of Embodiment 8, so as to produce a divided type nonaqueous curable composition including these agents in a weight ratio of 1:1. This divided type aqueous curable composition was subjected to the curing time test (P2) described below for obtaining a curing time and was also subjected to the shear bond strength test (Q3) described below for obtaining shear bond strength. The results are listed in Table 5 below.

Agent D2-2:

| Bis-GMA | 40 parts by weight |
|---|---|
| HEMA | 40 parts by weight |
| TEGDMA | 20 parts by weight |
| DEPT | 1 part by weight |
| TPBSS | 1 part by weight |
| Silanated quartz filler | 300 parts by weight |

[Curing Time Test (P2)]

The agents D1-1 and D1-2 or D2-2 were respectively weighed out by 0.2 g and mixed with a spatula so as to give a paste. This paste was immediately placed in a hemispherical plastic vessel with a diameter of 1 cm and a depth of 5 mm, and a thermocouple (manufactured by Okazaki Manufacturing Company) connected to a recorder (manufactured by Yokogawa Electric Corporation) was inserted into the paste, so as to record temperature change caused in a polymeric curing reaction with the recorder, and a curing time (time elapsed from the mixing to a rise of an exothermic peak) was thus obtained.

[Shear Bond Strength Test (Q3)]

The labial surface of a lower anterior tooth of a bovine was polished with #80 silicon carbide paper (manufactured by Nihon Kenshi Co., Ltd.) in running water so as to form two kinds of flat surfaces of an enamel and a dentine. A dental composite resin was loaded in a stainless steel cylinder having a bottom closed with a bottom cover, and the bovine lower anterior tooth was buried in the dental composite resin so as not to immerse the flat surface. After curing the composite resin, the bottom cover was removed, and the exposed flat surface was further polished with #1000 silicon carbide paper (manufactured by Nihon Kenshi Co., Ltd.) in running water so as to form a smooth surface. An adhesive tape with a thickness of approximately 150 μm having a hole with a diameter of 4 mm was adhered onto the smooth surface for restricting an adhesion area. Subsequently, a cylindrical polytetrafluoroethylene mold with an inner diameter of 4 mm and a height of 2 mm was placed on the hole (adhesion surface), and the mold was filled with a paste obtained by mixing the agents D1-1 and D1-2 or D2-2. One hour after filling the paste, the cylindrical polytetrafluoroethylene mold was removed, thereby giving the resultant as a test piece. The test piece was immersed in water of a temperature of 37° C. and was taken out of the water after 24 hours, and shear bond strength was measured with a universal testing machine (manufactured by Instron Corporation). The shear bond strength was measured with a cross head speed set to 2 mm/min. An average of measured values obtained in eight test pieces was regarded as the shear bond strength of the test pieces.

TABLE 5

|  |  | Embodiment 8 | Comparative Example 6 |
|---|---|---|---|
| Curing time |  | 5 min. 20 sec. | 6 min. 00 sec. |
| Shear Bond | Enamel | 22.8 | 15.8 |
| Strength (MPa) | Dentine | 15.6 | 5.3 |

As shown in Table 5, the present composition produced in Embodiment 8 had a practical curing time and exhibited high adhesive strength against both an enamel and a dentine. On the other hand, the nonaqueous curable composition produced in Comparative Example 6 had low adhesive strength against a dentine. The adhesive strength against a dentine of the nonaqueous curable composition produced in Comparative Example 6 was low probably for the following reason: Since reducing compounds dissolving in the composition (DEPT and TPBSS) were used as reductants of the redox polymerization initiator, there was a high frequency of encounter in a molecular state between the organic peroxide and the reducing compounds in the composition, and the amount of reducing compounds distributing the polymeric curing reaction on the adhesion interface was reduced, and hence, the nonaqueous curable composition was not sufficiently polymerically cured on the adhesion interface. On a dentine in which the polymerization inhibition is easily caused by oxygen present in the dentine, the adhesiveness is largely lowered.

(Embodiment 9)

Agents E1-1 and E1-2 having compositions described below were prepared and combined, so as to produce a divided type nonaqueous curable composition (present composition) including these agents in a weight ratio of 1:1. In the composition obtained by mixing the agents E1-1 and E1-2, sodium sulfite was in a dispersed state. This divided type nonaqueous curable composition was subjected to the aforementioned curing time test (P2) for obtaining a curing time and was also subjected to a shear bond strength test (Q4) described below for obtaining shear bond strength. The results are listed in Table 6 below.

Agent E1-1:

| Bis-GMA | 40 parts by weight |
|---|---|
| HEMA | 20 parts by weight |
| TEGDMA | 20 parts by weight |
| MDP | 20 parts by weight |
| BPO | 1 part by weight |
| Silanated quartz filler | 300 parts by weight |

Agent E1-2:

| Bis-GMA | 40 parts by weight |
|---|---|
| HEMA | 40 parts by weight |
| TEGDMA | 20 parts by weight |
| Sodium sulfite powder (with an average particle diameter of 6.1 μm) | 4 parts by weight |
| DEPT | 1 part by weight |
| TPBSS | 1 part by weight |
| Aluminofluorosilicate glass GM35429 (manufactured by Schott) | 300 parts by weight |

COMPARATIVE EXAMPLE 7

An agent E2-2 having a composition described below was prepared by excluding the sodium sulfite powder from the agent E1-2 of Embodiment 9, and the agent E2-2 was combined with the agent E1-1 of Embodiment 9, so as to produce a divided type nonaqueous curable composition including these agents in a weight ratio of 1:1. This divided type aqueous curable composition was subjected to the aforementioned curing time test (P2) for obtaining a curing time and was also subjected to the shear bond strength test (Q4) described below for obtaining shear bond strength. The results are listed in Table 6 below.

Agent E2-2:

| Bis-GMA | 40 parts by weight |
|---|---|
| HEMA | 40 parts by weight |
| TEGDMA | 20 parts by weight |
| DEPT | 1 part by weight |
| TPBSS | 1 part by weight |
| Aluminofluorosilicate glass GM35429 (manufactured by Schott) | 300 parts by weight |

[Shear Bond Strength Test (Q4)]

The labial surface of a lower anterior tooth of a bovine was polished with #80 silicon carbide paper (manufactured by Nihon Kenshi Co., Ltd.) in running water so as to form two kinds of flat surfaces of an enamel and a dentine. A dental composite resin was loaded in a stainless steel cylinder having a bottom closed with a bottom cover, and the bovine lower anterior tooth was buried in the dental composite resin so as not to immerse the flat surface. After curing the composite resin, the bottom cover and the stainless steel cylinder were removed, and the exposed flat surface was further polished with #1000 silicon carbide paper (manufactured by Nihon Kenshi Co., Ltd.) in running water so as to form a smooth surface. An adhesive tape with a thickness of approximately 150 μm having a hole with a diameter of 4 mm was adhered onto the smooth surface for restricting an adhesion area. Thereafter, a primer composition including 65 parts by weight of water, 25 parts by weight of HEMA and 10 parts by weight of MDP was applied within the hole with a brush, and the resultant was allowed to stand for 30 seconds and then dried with an air syringe until the primer composition lost its flowability. Subsequently, a cylindrical polytetrafluoroethylene mold with an inner diameter of 4 mm and a height of 2 mm was placed on the hole (adhesion surface), and the mold was filled with a paste obtained by mixing the agents E1-1 and E1-2 or E2-2. One hour after filling the paste, the cylindrical polytetrafluoroethylene mold was removed, thereby giving the resultant as a test piece. The test piece was immersed in water of a temperature of 37° C. and was taken out of the water after 24 hours, and shear bond strength was measured with a universal testing machine (manufactured by Instron Corporation). The shear bond strength was measured with a cross head speed set to 2 mm/min. An average of measured values obtained in eight test pieces was regarded as the shear bond strength of the test pieces.

TABLE 6

| | | Embodiment 9 | Comparative Example 7 |
|---|---|---|---|
| Curing time | | 4 min. 50 sec. | 5 min. 15 sec. |
| Shear Bond | Enamel | 25.8 | 20.0 |
| Strength (MPa) | Dentine | 17.9 | 6.8 |

As shown in Table 6, the present composition produced in Embodiment 9 had a practical curing time and exhibited high shear bond strength against both an enamel and a dentine. On the other hand, the nonaqueous curable composition produced in Comparative Example 7 had low shear bond strength against a dentine. The shear bond strength against a dentine of the nonaqueous curable composition produced in Comparative Example 7 was low probably for the following reason: Since reducing compounds dissolving in the composition (DEPT and TPBSS) were used as reductants of the redox polymerization initiator, there was a high frequency of encounter in a molecular state between the organic peroxide and the reducing compounds in the composition, and the amount of reducing compounds distributing the polymeric curing reaction on the adhesion interface was reduced, and hence, the nonaqueous curable composition was not sufficiently polymerically cured on the adhesion interface. On a dentine in which the polymerization inhibition is easily caused by oxygen present in the dentine, the adhesiveness is largely lowered.

The invention claimed is:

1. A biological hard tissue adhesive comprising a composition comprising:
   at least one liquid monomer (a);
   an organic peroxide (b); and
   a sulfite (c) having an average particle diameter of from 0.01 to 100 μm as a reducing agent,
   wherein
   the composition is dividedly packed as a first agent comprising said liquid monomer (a) and said organic peroxide (b) and a second agent comprising said at least one liquid monomer (a) and said sulfite (c) which is dispersed in the liquid monomer (a) of the second agent in the form of a solid,
   when the first agent and the second agent are in a mixed state so as to form a bulk composition, said sulfite (c) is dispersed in liquid monomer (a) in the form of a solid in the bulk composition,
   the reducing agent in the second agent consists of the sulfite (c),
   the composition does not contain water, and
   the composition does not contain: i) a polymeric monomer having at least one phosphoric acid group; or ii) a polymeric monomer represented by formula (I)

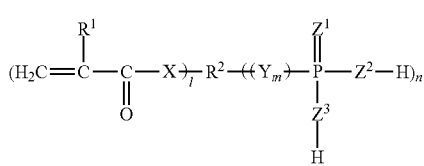

(I)

where $R^1$ is hydrogen or a methyl group, $R^2$ is a (1+n)-valent group with a carbon number of 2 to 40, l is an integer of 1 to 5, m is 0 or 1, n is an integer of 1 to 4, —X— is —O— or —NH—, —Y— is —O— or —S—, and $Z^1$, $Z^2$ and $Z^3$ are independently an oxygen atom or a sulfur atom.

2. The biological hard tissue adhesive according to claim 1, wherein said organic peroxide is selected from the group consisting of benzoyl peroxide; 2,4-dichlorobenzoyl peroxide; m-toluoyl peroxide; t-butyl peroxybenzoate; bis-t-butyl peroxyisophthalate; 2,5-dimethyl-2,5-bis (benzoylperoxy)hexane; t-butyl peroxy-2-ethyl hexanoate; t-butyl peroxyisopropyl carbonate; dicumyl peroxide; di-t-butyl peroxide; lauroyl peroxide; 1,1-bis(t-butyl peroxy)3,3,5-trimethyl cyclohexane; 1,1-bis(t-butyl peroxy)cyclohexane; 1,1-bis(t-hexyl peroxy) cyclohexane; methyl ethyl ketone peroxide; cyclohexanone peroxide; methyl acetoacetate peroxide; t-butyl hydroperoxide; cumene hydroperoxide; and p-diisopropyl benzene peroxide.

3. The biological hard tissue adhesive according to claim 1, wherein said sulfite (c) is a compound having a solubility in water of 1 mg/100 mL or more.

4. The biological hard tissue adhesive according to claim 1, wherein said sulfite (c) is selected from the group consisting of sodium sulfite; potassium sulfite; calcium sulfite; ammonium sulfite; sodium hydrogensulfite; and potassium hydrogensulfite.

5. The biological hard tissue adhesive according to claim 1, wherein said at least one liquid monomer (a) is at least one member selected from the group consisting of methyl (meth) acrylate; ethyl (meth)acrylate; propyl (meth)acrylate; isopropyl (meth)acrylate; butyl (meth)acrylate; isobutyl (meth) acrylate; benzyl (meth)acrylate; lauryl (meth)acrylate; 2,3-dibromopropyl (meth)acrylate; 2-hydroxyethyl (meth) acrylate; 2-hydroxypropyl (meth)acrylate; 3-hydroxypropyl (meth)acrylate; 1,3-dihydroxypropyl (meth)acrylate; 2,3-dihydroxypropyl (meth)acrylate; 2-hydroxyethyl (meth)acrylamide; 3-methacryloyloxypropyl trimethoxysilane; 11-methacryloyloxyundecyl trimethoxysilane; (meth)acrylamide; ethylene glycol di(meth)acrylate; triethylene glycol di(meth)acrylate; propylene glycol di(meth)acrylate; polyethylene glycol di(meth)acrylate having nine or more oxyethylene groups; neopentyl glycol di(meth)acrylate; 1,6-hexanediol di(meth)acrylate; 1,10-decanediol di(meth)acrylate; dipentaerythritol di(meth)acrylate; bisphenol A diglycidyl (meth)acrylate; 2,2-bis[4-(meth)acryloyloxyethoxyphenyl] propane; 2,2-bis[4-(meth)acryloyloxypolyethoxyphenyl] propane; 2,2-bis[4-[3-(meth)acryloyloxy-2-hydroxypropoxy]phenyl]propane; 1,2-bis[3-(meth)acryloyloxy-2-hydropropoxy]ethane; pentaerythritol di(meth)acrylate; 1,2-bis(3-methacryloyloxy-2-hydroxypropoxy)ethane; [2,2,4-trimethylhexamethylene bis(2-carbamoyloxyethyl)] dimethacrylate; 1,3-di(meth)acryloyloxy-2-hydroxypropane; trimethylolpropane tri(meth)acrylate; trimethylolethane tri(meth)acrylate; tetramethylolmethane tri(meth)acrylate; pentaerythritol tetra(meth)acrylate; N,N' -(2,2,4-trimethylhexamethylene) bis [2-(aminocarboxy)propane- 1, 3 -diol] tetramethacrylate; and 1,7-diacryloyloxy-2,2,6,6-tetraacryloyloxymethyl-4-oxyheptane.

6. The biological hard tissue adhesive according to claim 1, wherein the composition comprises
   100 parts by weight of said at least one liquid monomer (a);
   0.05 to 10 parts by weight of said organic peroxide (b); and
   0.01 to 15 parts by weight of said sulfite (c).

7. A composition comprising:
   100 parts by weight of a liquid monomer (a) that consists of at least one member selected from the group consisting of 2,2-bis[4-(3-methacryloyloxy-2-hydroxypropoxy)

phenyl] propane, triethylene glycol dimethacrylate, neopentyl glycol dimethacrylate, and 2-hydroxyethyl methacrylate;

0.05 to 10 parts by weight of an organic peroxide (b) that comprises benzoyl peroxide; and 0.01 to 15 parts by weight of a sulfite (c) having an average particle diameter of from 6.1 to 9.9 μm as a reducing agent, wherein the sulfite (c) present in the bulk of the composition is present in the form of a solid dispersed in the liquid monomer (a), the sulfite (c) present at an interface between the composition and the dentin is present in solvated form and solvated by water from the dentin, the bulk of the composition does not contain water, the reducing agent in the liquid monomer (a) consists of the sulfite (c), the polymer obtained from polymerizing said liquid monomer (a) is a polymer having units of 2,2-bis[4-(3-methacryloyloxy-2-hydroxypropoxy)phenyl] propane, triethylene glycol dimethacrylate, neopentyl glycol dimethacrylate, 2-hydroxyethyl methacrylate, or a combination thereof, the bonding strength between the composition and dentin, when the composition is present on and bound to dentin, is from 12.0 to 17.9 MPa, and the composition does not contain: i) a polymeric monomer having at least one phosphoric acid group; or ii) a polymeric monomer represented by formula (I)

$$(H_2C=\overset{R^1}{\underset{\underset{O}{\|}}{C}}-C-X)_l-R^2-(\!(Y_m)\!)-\overset{\overset{Z^1}{\|}}{\underset{\underset{H}{\overset{Z^3}{|}}}{P}}-Z^2-H)_n \qquad (I)$$

where $R^1$ is hydrogen or a methyl group, $R^2$ is a (1+n)-valent group with a carbon number of 2 to 40, l is an integer of 1 to 5, m is 0 or 1, n is an integer of 1 to 4, —X— is —O— or —NH—, —Y— is —O— or —S—, and $Z^1$, $Z^2$ and $Z^3$ are independently an oxygen atom or a sulfur atom.

8. A composition according to claim 7, wherein the composition is in a cured state.

9. A composition according to claim 7, wherein said liquid monomer (a) comprises 2,2-bis[4-(3-methacryloyloxy-2-hydroxypropoxy)phenyl] propane.

10. A composition according to claim 7, wherein said liquid monomer (a) comprises triethylene glycol dimethacrylate.

11. A composition according to claim 7, wherein said liquid monomer (a) comprises neopentyl glycol dimethacrylate.

12. A composition according to claim 7, wherein said liquid monomer (a) comprises 2-hydroxyethyl methacrylate.

13. A biological hard tissue adhesive composition, comprising:

100 parts by weight of a liquid monomer (a) that comprises at least one member selected from the group consisting of 2,2-bis[4-(3-methacryloyloxy-2-hydroxypropoxy) phenyl] propane, triethylene glycol dimethacrylate, neopentyl glycol dimethacrylate, and 2-hydroxyethyl methacrylate;

0.05 to 10 parts by weight of benzoyl peroxide; and 0.01 to 15 parts by weight of a sulfite (c) having an average particle diameter of from 6.1 to 9.9 μm as a reducing agent, wherein said liquid monomer (a) has a bulk portion and a perimeter portion where water is present in said perimeter portion, said bulk portion does not contain water said sulfite comprises at least one member selected from the group consisting of sodium sulfite; potassium sulfite; calcium sulfite; ammonium sulfite; sodium hydrogensulfite; and potassium hydrogensulfite, said reducing agent of the composition consists of sulfite (c), said sulfite is present in said bulk portion in the disperse phase, said sulfite is present in said perimeter portion in dissolved form and dissolved by said water present in said perimeter portion, and the composition does not contain: i) a polymeric monomer having at least one phosphoric acid group; or ii) a polymeric monomer represented by formula (I)

$$(H_2C=\overset{R^1}{\underset{\underset{O}{\|}}{C}}-C-X)_l-R^2-(\!(Y_m)\!)-\overset{\overset{Z^1}{\|}}{\underset{\underset{H}{\overset{Z^3}{|}}}{P}}-Z^2-H)_n \qquad (I)$$

where $R^1$ is hydrogen or a methyl group, $R^2$ is a (1+n)-valent group with a carbon number of 2 to 40, l is an integer of 1 to 5, m is 0 or 1, n is an integer of 1 to 4, —X— is —O— or —NH—, —Y— is —O— or —S—, and $Z^1$, $Z^2$ and $Z^3$ are independently an oxygen atom or a sulfur atom.

14. The biological hard tissue adhesive composition according to claim 13, wherein said sulfite comprises one of sodium sulfite and potassium sulfite.

15. The biological hard tissue adhesive composition according to claim 13, wherein said liquid monomer (a) comprises a mixture of 2,2-bis[4-(3-methacryloyloxy-2-hydroxypropoxy)phenyl] propane, triethylene glycol dimethacrylate, and 2-hydroxyethyl methacrylate.

16. A biological hard tissue adhesive comprising a composition comprising:

at least one liquid monomer (a);

an organic peroxide (b); and a sulfite (c) having an average particle diameter of from 0.01 to 100 μm, wherein the composition is dividedly packed as a first agent comprising said liquid monomer (a) and said organic peroxide (b) and a second agent comprising said at least one liquid monomer (a) and said sulfite (c) which is dispersed in the liquid monomer (a) of the second agent in the form of a solid, when the first agent and the second agent are in a mixed state so as to form a bulk composition, said sulfite (c) is dispersed in liquid monomer (a) in the form of a solid in the bulk composition, the composition does not contain water, and which does not contain a polymeric monomer represented by formula (I)

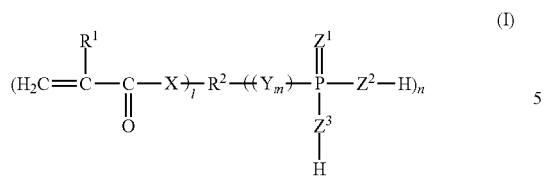
where $R^1$ is hydrogen or a methyl group, $R^2$ is a (1+n)-valent group with a carbon number of 2 to 40, l is an integer of 1 to 5, m is 0 or 1, n is an integer of 1 to 4, —X— is —O— or —NH—, —Y— is —O— or —S—, and $Z^1$, $Z^2$ and $Z^3$ are independently an oxygen atom or a sulfur atom.
* * * * *